United States Patent [19]

Brand et al.

[11] 4,031,320
[45] June 21, 1977

[54] SOUND PRODUCING DEVICE

[76] Inventors: Bridget A. Brand; Joseph Brand, both of 133 Drexel Road, Ardmore, Pa. 19003

[22] Filed: Mar. 19, 1976

[21] Appl. No.: 668,411

[52] U.S. Cl. .............................................. 179/1 AA
[51] Int. Cl.$^2$ ...................................... A61M 21/00
[58] Field of Search ................................ 179/1 AA

[56]  References Cited
UNITED STATES PATENTS

| | | | |
|---|---|---|---|
| 2,304,095 | 12/1942 | Hull | 179/1 AA |
| 3,213,851 | 10/1965 | Curren | 179/1 AA |
| 3,272,198 | 9/1966 | Balkin | 179/1 AA |

*Primary Examiner*—Kathleen H. Claffy
*Assistant Examiner*—E. S. Kemeny
*Attorney, Agent, or Firm*—Benasutti Associates, Ltd.

[57] ABSTRACT

An apparatus for inducing general relaxation and sleep is described which plugs into a regular electrical outlet and emits a low, but constant humming sound of barely audible amplitude within specified decibel ranges, frequency ranges, oscillatory amplitude ranges, and periodicity ranges. In the preferred embodiment of the device, a housing is provided having a plug protruding therefrom which enables the housing to cover an outlet to prevent small infants from receiving electrical shocks. An alternate embodiment is provided wherein the sound producing device further comprises a night light assembly.

7 Claims, 4 Drawing Figures

SOUND PRODUCING DEVICE

BACKGROUND OF THE INVENTION

Noise pollution in our cities is an increasingly serious problem. Experts are now beginning to realize that in addition to the physical damage sounds can do to hearing, loud sounds have several other physical effects. Sounds in the range of 140 decibels—the level that is reached a few feet from the catapult of an aircraft carrier—produce a number of unpleasant bodily sensations: a feeling of vibration inside the head, severe pain in the middle ear, loss of equilibrium, and nausea. Certain low frequency sound is likely to produce a startle reaction wherein norepinephrine and other body hormones are released for the purpose of preparing the body to respond to an emergency. The startle reaction causes the blood pressure and the pulse rate to jump, the muscles to contract, perspiration to increase, the flow of saliva and gastric juices to reduce, and digestion to cease.

Noted experts in the field of sound, such as C. P. Boner claim that the sound to which urban dwellers are exposed contribute to circulatory troubles, loss of hearing, fatigue, and emotional disturbances. In particular, others in the field believe that the average urban dweller is subjected to stress, particularly because he is unable to get prolonged, uninterrupted sleep. In fact, urban street noise has been measured to range between 80 decibels on the quieter main streets in the smaller cities, to a maximum of approximately 109 decibels a few feet from an accelerating diesel bus.

The home itself is, of course, increasingly an independent source of sound, particularly from such appliances as dishwashers, garbage disposals, and vacuum cleaners. These appliances create noises in the vicinity of 60 to over 100 decibels.

It has long been known that it is possible to fight noise with white noise. White noise is often compared to the soft rush of escaping steam. White noise is often used to convert disturbing silence into controlled quiet as well as to mask noises which would otherwise by distracting. White noise is now commonly used in dentistry to mask nervewracking drilling noise thereby removing much of the tension, anxiety and pain associated with the drilling operation.

The need for effective noise elimination or masking is quite pervasive. Psychologists Sheldon Cohen, David Glass, and Jerome Singer claim that young children may suffer impaired learning ability due to the continual background din from their living close to a busy highway which makes it difficult to discriminate home conversations, and therefore, their understanding of words. According to the National Research Council of Canada, 35-million Americans live in areas where 24-hour noise averages 65 decibels—annoying if not necessarily harmful— and 90% of our population is subject to sporadic and "intrusive" sounds that exceed 75 decibels. The World Health Organization estimates that noise costs the United States 4-billion dollars annually in accidents, absenteeisms, and compensation claims.

Of course, in addition to the loudness of the particular sounds, it has been speculated that those sounds which intermittently interrupt everyday activities may in fact, be the most harmful. Pschologist Howard M. Brogard has theorized that the most harmful noises are those that invade one's dreams, because dreaming is necessary for mental health. When the dream is interrupted by a jet plane, a fire engine, or a noisy neighbor, the person will dream twice as much the next night. But if he is interrupted again and again, he will become emotionally upset. It has been speculated that this is the explanation for the relatively high admittance to mental hospitals which has been found for residential areas surrounding airports such as Heathrow Terminal outside London. It is theorized therefore that people will actually sleep better when subjected to heavy but regular traffic outside their windows than when the traffic is lighter but unpredictable.

Although the obvious answer to the noise pollution problem is to reduce the noise to which we are all subjected, the Environmental Resources Agency contends that it will take until the end of the century to shave five decibels off the sonic environment. It has been estimated that to lower the industrial noise level by five decibels would cost from between eight and thirty-one billion dollars. These and other problems relating to the area of noise pollution are discussed in S. S. Stevens and Fred Warshofsky, SOUND AND HEARING, 1965, Time-Lift Books, Inc., New York; New York Times Magazine, VI (Nov. 23, 1965), "Noise," by David Dempsey, pp. 31ff; and PHYSIOLOGY AND BIOPHYSICS, edited by T. C. Ruch and H. D. Patton, 1965, W. B. Saunders and Company, Philadelphia, 19th edition, Chapter 18, pp. 379–384.

It has long been known that one sound may be obscured or masked by another. The most commonly used masking stimulus is white noise, noise with a uniform power spectrum from one extreme of its frequency range to the other. It is also known to attempt to directly mask a tone by producing a second signal relatively close to that tone. In this case, beats are produced between the frequency of the primary and the frequency of the masking tones unless those tones are of too short a duration to permit a full cycle of beating to occur or, alternatively, if a narrow band of noise rather than a tone is used as a masking sound. Although it has been suggested that there are critical bands for masking tones which act to activate a particular filter response in the ear which preempts a particular band width and therefore, recognition of the sound to be masked, these theories are not yet definitive, particularly in view of the widely recognized phenomenon of remote masking. First discovered by Bilger and Hirsh in 1956, remote masking is clearly present when high noise levels such as 60 to 80 db are used to mask frequencies below those of the band of masking noise. For example, a band of noise from 2450 to 3120 Hertz (Hz) at a spectral level of about 70 db will elevate the threshold for tones from 100 to 1000 Hz by about 20 db. Although not yet definitively understood, other factors which appear to play a part in masking are temporal qualities, such as the duration between the occurrance of the masking tone and the tone to be masked (either forward or backward), the distribution of the noise and noise plus signal, the energy band width and duration, and the signal or frequency uncertainty of the masking tone. A complete discussion of these and other masking criteria is found in FOUNDATIONS OF MODERN AUDITORY THEORY, edited by Jerry V. Tobias, 1970, Academic Press, New York, Chapter 3, "Masking," by Lloyd A. Jeffress, pp. 87–114.

SUMMARY OF THE INVENTION

The present invention provides a novel device which emits a low, but constant, humming sound, which sound is of a decibel range of between 20 to 50 decibels and a frequency of between 200 and 500 cps, said sound being comprised of at least two and preferably, five major components within the range of 200 to 350 cps with no filters to capture the overtones above 400 and less than 500 cps, but filtered to avoid any substantial components over 500 or under 200 cps. The tone is further slightly pulsating, periodic, or oscillating but of relatively constant amplitude, its oscillation in terms of cps percentages being more than ±5% and less than ±20% and preferably appoximately ±10%. The oscillations or beats are preferably sinusoidal having peaks occurring between once every one to five seconds.

A sound as described above, when adjusted to a barely audible volume depending upon the environmental installation, will provide an extremely soothing, relaxing and sleep inducing environment. Although applicants do not wish to be bound by any particular theory, it is believed that a form of remote masking occurs prior to or during sleep wherein sound of the above described nature is particularly effective in masking relatively higher frequency and higher amplitude noises. The periodicity of the frequency variation and the relatively low amplitude of the noise is believed to provide considerable signal uncertainty which, together with the plurality of components which characterize the noise exhibit an unusually broad masking phenomenon.

In addition to providing an extremely efficient masking noise, applicants' invention provides a device which is particularly suited for home use. A relatively compact housing appropriately fitted to uniformly radiate the sound as provided which device may further act to shield electrical sockets from small infants, thereby preventing shock therefrom. Additionally, an alternate embodiment of the present invention is provided, combining the above described features together with the night light to provide a novel device, suitable for use in a bedroom.

Accordingly, a primary object of the present invention is the provision of a device for inducing relaxation and sleep; another object of the present invention is the provision of a device for masking extraneous sounds; a further object of the present invention is the provision of a sleep inducing night light; these and other objects of the present invention will become apparent from the following, more detailed, description of the drawings.

DETAILED DESCRIPTION OF THE DRAWINGS

Figure 1:
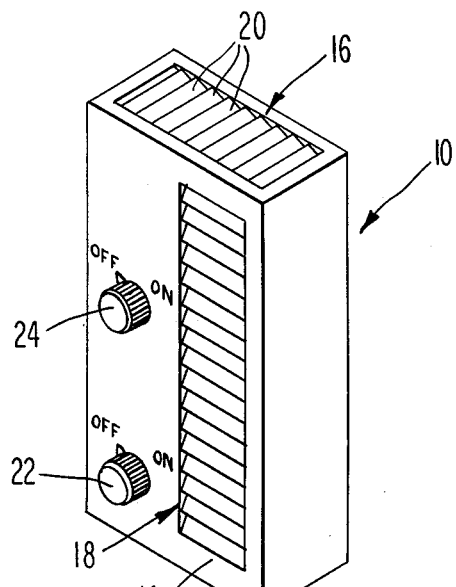
FIG. 1 is a front perspective view taken from the top left-hand side of the preferred embodiment of the present invention.

Although specific forms of the invention have been selected for illustration in the drawings, and the following description is drawn in specific terms for the purpose of describing these forms of the invention, this description is not intended to limit the scope of the invention which is defined in the appended claims.

As illustrated in FIG. 1, the preferred embodiment of the present invention is a small, substantially rectangular box-shaped device generally comrising a housing 10. This housing which is approximately one-inch thick, is approximately as long and as wide as a standard wall socket cover, the function of which will become apparent from the following description. Along the top 12 and front 14 of housing 10 are disposed two substantially rectangular sound ventilating channels designated generally, 16 and 18. Within these channels are a plurality of louvers 20 which are angled with respect to front and side surfaces so as to allow the radiation of sound therethrough while preventing the introduction of foreign objects into the device. Disposed on the front surface 14 of the housing 10 are controls 22 and 24. Although only two controls are shown in FIG. 1, it will be understood that is is within the purview of the present invention to provide a suitable number and type of control on this front surface 14 to accomplish the desired functions as more fully described hereinafter.

Figure 2:
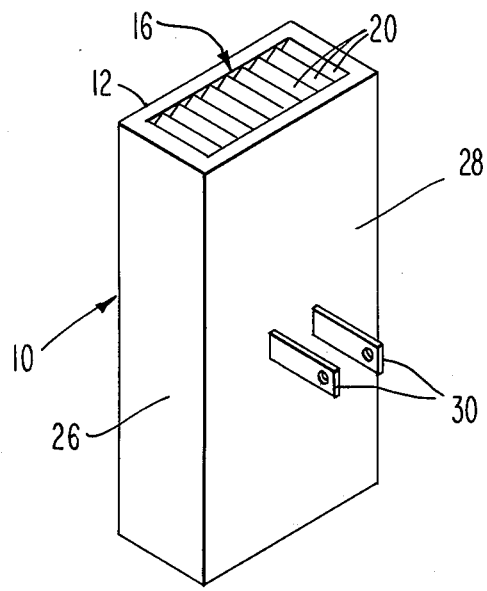
FIG. 2 is a back perspective view taken from the top left-hand side of the device illustrated in FIG. 1.

Referring to FIG. 2, the preferred embodiment of the present invention is shown in a back perspective view taken from the top left-hand side. Sound ventilating channels designated generally 16 with louvers 20 disposed therein are shown disposed within top surface 12. Side panel 26 and back panel 28 are visible in FIG. 2. Prongs 30 for interconnection with conventional wall outlet are illustrated as being relatively centered in FIG. 2, however, it is also within the purview of the present invention to offset prongs 30 relatively towards one end or the other of housing 10 so that, depending upon the orientation of the device when it is inserted into the wall outlet, the other of the two outlets conventionally found may alternatively be free or protected. In a further alternate embodiment of my device it is contemplated that prongs 30 may be mounted for rotation about their parallel bisectional axis, thereby allowing the device to be rotated in the event that the second receptacle outlet need be utilized.

Figure 3:
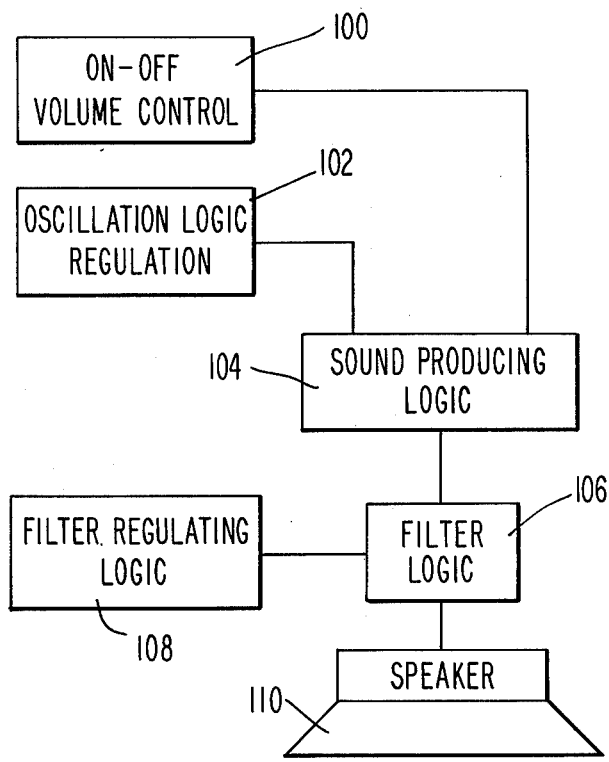
FIG. 3 is a diagrammatic illustration of the circuitry disposed within the preferred embodiment of the present invention.

Referring now to FIG. 3, the electronic circuitry disposed within the preferred embodiment is diagrammatically illustrated. As is described above, the preferred embodiment is designed to produce sound within a decibel range of 20 to 50 decibels, which range is set at a barely audible level by the user, depending upon the surrounding environment. The preselected volume is regulated by the off/on volume controls illustrated in block 100.

A second type of regulation which is provided in the preferred embodiment of the present invention is oscillation logic regulation, which logic has the effect of regulating the sound producing logic 104 so that a sinusoidal oscillation of the tones produced will occur, which oscillation will range from between ±5% to ±20%, and preferably ±10%. The duration between sinusoidal peaks ranges from between 1 to 5 seconds, which regualtion and frequency deviation may be controlled by the oscillation logic regulation 102 to suit the preferences of the user. Sound producing logic 104 is provided which logic comprises the plurality of sound generators which, in combination with the volume control, produce a total amplitude after filtration which does not vary more than ±5%. This sound producing logic comprises a number of tone generators for producing a plurality of tones within the range of 200 to 500 cps, which tones have their major amplitudes, preferably 60% or more, within the 200 to 350 cps range with overtones ranging between 400 to 500 cps. Filter logic 106 is utilized in order to modify the output of sound producing logic 104 and to limit the sound produced to within the preferred 200 to 500 cps range. Therefore, sound producing logic 104 may be simply and inexpensively constructed using oscillators which produce overtones substantially out of the desired range, which overtones and seondary tones are then filtered by filter logic 106. In the preferred embodiment, filter regulator logic is provided to allow the timbre of the sound to be altered either by changing the relative amplitude proportions of those tones between 200 and 350 cps and those between 350 and 500 cps, or by expanding the band width of the sounds produced to include overtones to as high as 1000 cps. Speaker 110 is provided disposed within the housing in a suitable position with respect to sound ventilating channels 16 and 18 to provide good sound dispersion into the room.

Figure 4:
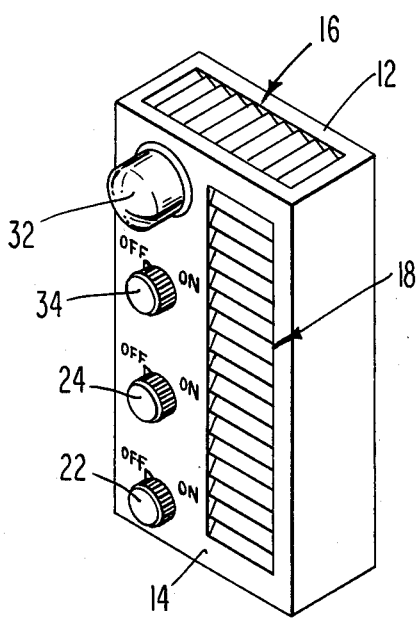
FIG. 4 is a front perspective view taken from the top left-hand side of the sleep inducing night light embodiment of the present invention.

Referring now to FIG. 4, the sleep inducing night light embodiment of the present invention is illustrated similarly having sound ventilating channels, designated generally 16 and 18 on the top 12 and front 14 thereof and also having a dome 32 operable by control 34 in which dome is disposed a suitable night light for dim illumination of the sleeping chamber.

The device of the present invention provides an extremely efficient and soothing noise masking sound. The fact that a relatively slow, periodic oscillation of the frequency is provided prevents annoying beats from developing between the masking sound and the sound to be masked. Futhermore, the setting of the volume at a barely audible frequency tends to act together with this periodic oscillation to produce a sound of relatively constant amplitude in which there is considerable tonal uncertainty. The nature of the sound is relatively dull and monotonous, yet not so pervasive as to become oppressive to the subject attempting to go to sleep. It is believed that the device is particularly useful with infants and small children who might otherwise be frightened or disturbed by sudden bursts of unwanted noise.

It will be understood that various changes in the details, materials and arrangement of parts which have been herein described and illustrated in order to explain the nature of this invention may be made by those skilled in the art within the principle and scope of the invention as expressed in the following claims.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:
1. An apparatus for inducing general relaxation and sleep comprising:
 a. a housing having sound ventilating channels disposed therethrough; and
 b. a sound producing means disposed within said housing for producing low frequency, periodic oscillatory sound of barely audible amplitude, said sound producing means producing a pre-selected sound having any of a variety of amplitudes between 20 and 50 and decibels, said pre-selected amplitude being controlled to within ±5 decibel percent, during said oscillatory sound period whereby a soft background level is attained which masks infrequent yet annoying bursts of consciously perceived noise.
2. The apparatus of claim 1 wherein said sound producing means produces a pre-selected sound of sinusoidal character in which the frequency variation is more than ±5 and less than ±20 cps percent, the sinusoidal peaks of said frequency variation occurring between 1 and 5 seconds apart.
3. The invention of claim 1 wherein said sound producing means produces a pre-selected sound within the range of 200 to 500 cps, more than 50% of the amplitude of said sound being composed of a plurality of tones in the range of 200 to 350 cps.
4. The claim 1 sound producing apparatus for inducing general relaxation and sleep for use with a covered wall outlet having a plurality of sockets thereon, said housing comprising a substanially rectangular, box-shaped housing having a length and width of the back surface thereof at least as great as said covered socket; said back surface having protruding therefrom two prongs for insertion into said wall socket, said prongs being located on said housing so that upon insertion of said prongs into said socket, said housing may selectively cover any remaining sockets of said outlet.
5. The invention of claim 4 wherein said apparatus further comprises a light emitting means for providing dim illumination to a sleeping chamber.
6. The invention of claim 1 wherein said sound producing means produces a pre-selected sound, at least 50% of the amplitude of which is within the frequency range of 200 to 350 cps, and wherein said sound producing means further comprises means for varying the timbre of said sound comprising control means for varying the bandwidth of the remainder of said amplitude selectively from 350 to between 500 and 1000 cps.
7. The invention of claim 1 wherein said sound producing means produces a pre-selected sound, at least 50% of the amplitude of which is within the frequency range of 200 to 350 cps, and wherein said sound producing means further comprises control means for selectively varying said percentage over 50%, with the remainder of said amplitude percentage of said sound being within the range of 350 to 500 cps.

* * * * *